US00PP17553P2

(12) United States Plant Patent
Austin

(10) Patent No.: US PP17,553 P2
(45) Date of Patent: Apr. 3, 2007

(54) SHRUB ROSE PLANT NAMED 'AUSTANGO'

(50) Latin Name: *Rosa hybrida*
Varietal Denomination: AUStango

(75) Inventor: David C. H. Austin, Albrighton (GB)

(73) Assignee: David Austin Roses Limited, Albrighton (GB)

( * ) Notice: Subject to any disclaimer, the term of this patent is extended or adjusted under 35 U.S.C. 154(b) by 0 days.

(21) Appl. No.: 11/263,875

(22) Filed: Oct. 31, 2005

(51) Int. Cl.
*A01H 5/00* (2006.01)

(52) U.S. Cl. ..... Plt./105

(58) Field of Classification Search ..... Plt./105, Plt./106, 107
See application file for complete search history.

*Primary Examiner*—Kent Bell
*Assistant Examiner*—June Hwu
(74) *Attorney, Agent, or Firm*—Klarquist Sparkman LLP

(57) ABSTRACT

Shrub rose plant substantially as herein shown and described, characterized particularly by its repeat flowering in large, full cupped blooms of an unusual burnt orange color; having a strong mixed fruity fragrance with banana and tea on a tall, bushy and upright shrub and its disease resistance.

1 Drawing Sheet

Figure 1:
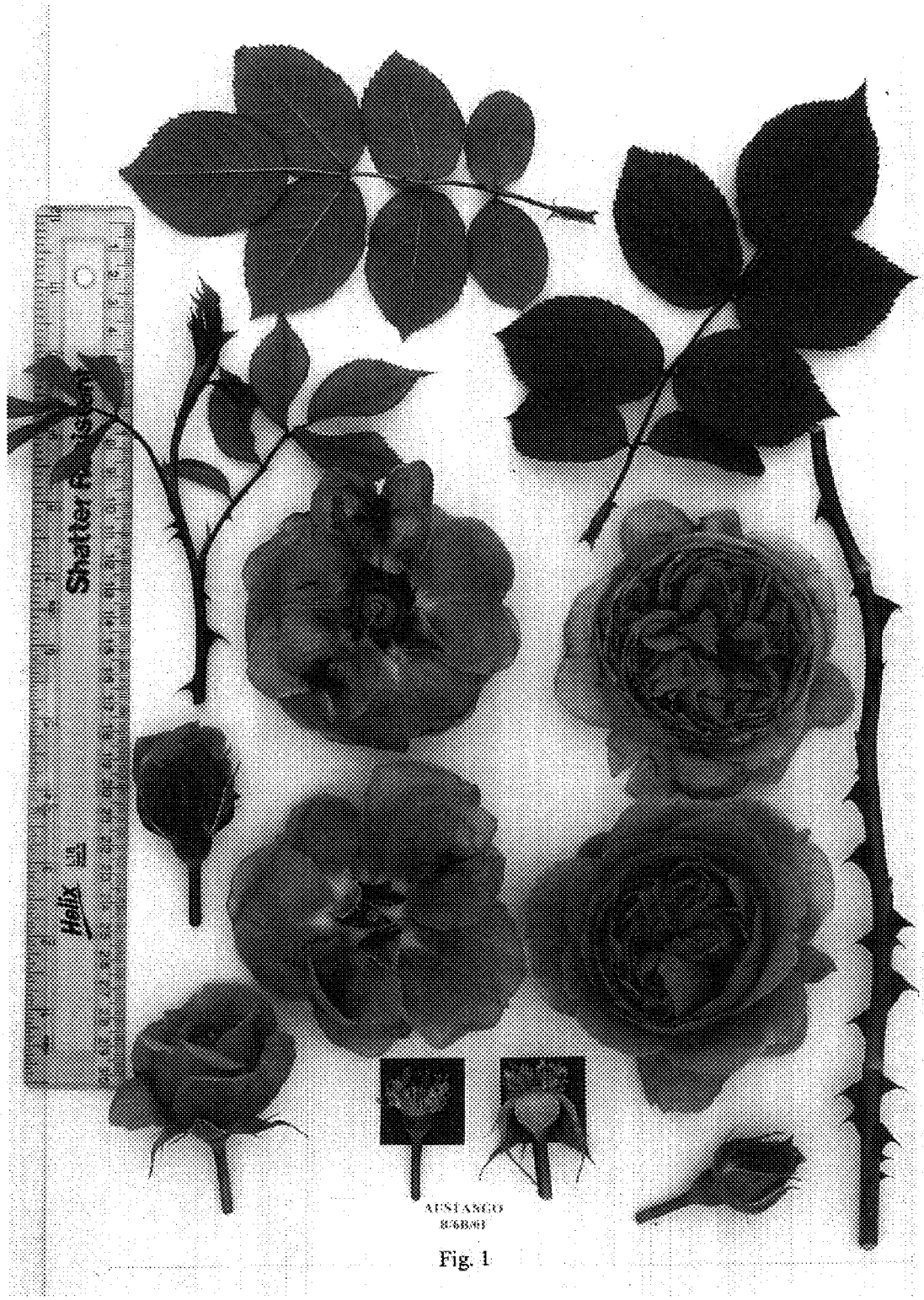

Genus and species: *Rosa hybrida.*
Variety denomination: 'AUStango'.

ORIGIN OF THE INVENTION

The present invention relates to a new and distinct variety of a shrub rose plant named 'AUStango' which was originated by me by crossing an unnamed, unpatented seedling with an unnamed, unpatented seedling.

BACKGROUND OF THE INVENTION

The primary objective of this breeding was to produce a bushy, upright shrub which repeat flowers well and bears large, full cupped blooms that are burnt orange in color.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Flowers in large, full cups of an unusual burnt orange color.
2. Tall, bushy and upright shrub.
3. Strong mixed fruity fragrance with banana and tea.

Asexual reproduction of this new variety by budding, as performed at Albrighton, England, shows that the foregoing and all other characteristics and distinctions come true to form and are established and transmitted through succeeding propagations.

Comparison with Parents

The seed parent has pink blooms in rosettes compared with the burnt orange, cupped blooms of 'AUStango' and has stronger growth. The pollen parent is a taller shrub than 'AUStango' and its blooms are pale pink rosettes.

Comparison with Similar Variety

'AUSmum' (U.S. Plant Pat. No. 9,527) has blooms that are brighter orange than those of 'AUStango' and mixed with yellow, and it makes a broader, more arching shrub. 'AUStango' has smaller leaves and fuller blooms than 'AUSmum'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character. The reference B/6B/01 appearing beneath the varietal name on the illustration is the applicant's breeding code for the cultivar.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling. (Unpatented).

FLOWER

Observations made from plants commencing at one year of age grown in a garden environment at Albrighton, England.

Blooming habit: Recurrent. The number of blooms per plant during the growing season is profuse, but there are too many to count.

Bud:
*Size.*—About 3.8 cm long and 2.1 cm in diameter when the petals start to unfurl.

*Form.*—The bud form is urceolate.

*Color.*—When sepals first divide, bud color is Red Group 42A. When half blown, the upper sides of the petals are Orange-Red Group 33B; and the lower sides of the petals are Orange-Red Group 34C with Red Group 45A at base.

*Sepals.*—Color: Lower surface: Some Red Group 53A, some Yellow-Green Group 144A with 144B at base. Upper surface: Yellow-Green Group 148C. Length: 2.8 cm. Width: 1.2 cm. Shape: Subulate. Surface texture: Lower surface: Smooth with strong raised central ridge running to apex. Upper surface: Pubescent. There are three normally appendaged sepals. There are two unappendaged sepals with canescent edges.

*Receptacle.*—Color: Green Group 143B with irregular patches of Red Group 53A. Shape: Campanulate. Size: Medium, about 1 cm long×1.2 cm wide. Surface: Smooth.

*Peduncle.*—Length: Medium, averaging about 8 cm. Surface: Glandular. Color: Yellow-Green Group 144B on shaded surface, Greyed-Purple Group 184A on surface exposed to sun. Strength: Normal to weak.

Bloom:

*Size.*—Large. Average open diameter is about 9.7 cm.

*Borne.*—Several together in rounded clusters of seven to nine blooms.

*Form.*—When first open: Cupped. Permanence: Retains its form.

*Petalage.*—Number of petals under normal conditions: 80–90.

*Color.*—The upper sides of the petals are Orange-Red Group 31B. The reverse sides of the petals are Orange-Red Group 35B. The bases of the petals are Yellow Group 9B on lower surface and Yellow Group 9A on upper surface. The major color on the upper sides is Orange-Red Group 31B.

*Variegations.*—None.

*Discoloration.*—The general tonality at the end of the first day: Orange-Red Group 35B. At the end of the third day: Red Group 37B upper side, Orange-Red Group 31C underside.

*Fragrance.*—Strong, fruity.

Petals:

*Texture.*—Smooth.

*Size.*—Width: 3.7 cm. Length: 5.3 cm.

*Surface.*—Smooth.

*Shape.*—Obdeltoid/broad elliptical. Margin: Flat, gentle undulation on inner petals, some slightly reflexing. Apex Shape: Rounded (some outer petals emarginated). Base Shape: Cuneate/Pointed. Form: Incurved, tips slightly recurved on some.

*Arrangement.*—Inner petals: Informal. Outer ring of petals: Imbricated.

*Petaloids.*—Number: 1. Anther: Color: Yellow-Orange Group 12C. Length: 1 mm. Filament: Color: Yellow-Orange Group 17A. Length: 7 mm. Petal: Color: Orange-Red Group 34A. Shape: Irregular. Length: 16 mm. Shape: Petal is joined to the filament, and anther is fused to margin of petal.

*Persistence.*—Petals drop off cleanly before drying.

*Lastingness.*—On the plant: Fair (about 4 days). As a cut flower: Short (about 4 days).

Reproductive parts:

*Stamens.*—Number: 35. Length: 11 mm. Anthers: Length: 3 mm. Color: Yellow-Orange Group 17A. Arrangement: Regular around styles. Filaments: Color: Red Group 42C. Length: 8 mm. Pollen: Color: Yellow-Orange Group 17A.

*Pistils.*—Number: 80. Length: 10 mm. Styles: Color: Green-White Group 157A with Orange-Red Group 35A below stigma. Length: 9 mm. Stigmas: Color: Yellow-Orange Group 14B. Length: 1 mm.

*Hips.*—None observed.

PLANT

*Form.*—Shrub.

*Growth.*—Medium vigor, upright, bushy.

*Age at maturity.*—Two years.

*Mature plant.*—Height: 1.25 m. Width: 0.9 m.

*Rootstock.*—'Dr. Huey' in the USA. *Rosa dumetorum* 'Laxa' for the observed plants in the U.K.

Foliage: Number of leaflets on normal mid-stem leaves: 5–7 (including terminal leaflet).

*Size.*—Large. About 19.4 cm long×14.5 cm wide.

*Quantity.*—Normal. Average number leaves per flowering stem: 12.

*Color.*—New foliage: Upper side: Yellow-Green Group 146A and Red Group 53A on margin. Lower side: Yellow-Green Group 146B. Old foliage: Upper side: Green Group 139A. Lower side: Yellow-Green Group 146A.

Leaflets:

*Size.*—About 7.6 cm long×5.2 cm wide.

*Shape.*—Pointed oval.

*Base shape.*—Rounded.

*Apex shape.*—Acuminate.

*Texture.*—Leathery.

*Edge.*—Serrated.

*Serrations.*—Single, large.

*Petiole.*—Color: Yellow-Green Group 144B. Surface texture: Smooth, a few glands present. Length: approximately 4 cm. Width: approximately 2 mm.

*Petiole rachis.*—Color: Yellow-Green Group 144B. Underside: Smooth (with a few glands).

*Stipules.*—Length: 1.9 cm. Margin: Glandular. Color: Greyed-Red Group 178A.

*Auricle shape.*—Elongated awl.

*Disease resistance.*—Resistant to powdery and downy mildew, blackspot and rust in normal growing conditions.

*Pest resistance.*—Not tested.

*Vein color.*—Yellow-Green Group 144B.

*Venation pattern.*—Reticulate.

Wood:

*New wood.*—Color: Greyed-Red Group 178A. Bark: Smooth.

*Old wood.*—Color: Yellow-Green Group 146B. Bark: Smooth.

Stems:

*Mature stem.*—Length: 45 cm. Diameter: 50 mm.

*Internode distance.*—4 cm. The above measurements are all variable, depending on growing conditions in a season.

Prickles:

*Quantity.*—On main canes from base: Ordinary, 4 per 10 cm stem length. On laterals from main canes: Ordinary, 5 per 10 cm per stem length.

*Form.*—Concave curved inward.

*Length.*—9 mm.

*Color when young.*—Greyed-Purple Group 185A with Yellow-Green Group 146D at tip.

*Color when mature.*—Greyed-Orange Group 164A at base, Greyed-Purple Group 184B at tip and along upper edge.

Small prickles:

*Quantity.*—On main stalks: None. On laterals: None.

Winter hardiness: Not tested.

I claim:

1. A new and distinct variety of shrub rose plant substantially as herein shown and described, characterized particularly by its repeat flowering in large, full cupped blooms of an unusual burnt orange color; having a strong mixed fruity fragrance with banana and tea on a tall, bushy and upright shrub and its disease resistance.

* * * * *